United States Patent [19]

Meilland

[11] Patent Number: Plant 6,792

[45] Date of Patent: May 9, 1989

[54] ROSE PLANT—MEIMAINGER VARIETY

[75] Inventor: Alain A. Meilland, Antibes, France

[73] Assignee: The Conard-Pyle Company, West Grove, Pa.

[21] Appl. No.: 135,071

[22] Filed: Dec. 18, 1987

[51] Int. Cl.[4] ..... A01H 5/00
[52] U.S. Cl. ..... Plt./17
[58] Field of Search ..... Plt./17

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms distinctive double blossoms which are vermilion orange on the upper surface and scarlet pink on the under surface. Such blossoms are formed in abundance and exhibit a spicy fragrance. The growth habit is regular, well-balanced, vigorous, dense, and erect, and the foliage is ornamental and glossy on the upper surface. Good resistance to cryptogamic diseases is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Meifiga variety by the Königin Der Rosen variety. The male parent (i.e., the pollen parent) of the new variety was formed by crossing the Meialfi variety by the Meitifran variety and crossing the resulting offspring by the King's Ransom variety (U.S. Plant Pat. No. 2,103). The parentage of the new variety can be summarized as follows:

[MEIFIGA × KÖNIGIN DER ROSEN]
×
[(MEIALFI × MEITIFRAN) × KING'S RANSOM].

The seeds resulting from the above pollination were sown and 86 plantlets were obtained which were physically and biologically different from each other. Selective study resulted in the identification of a single plant of the new variety.

It was found that the new variety of Hybrid Tea rose plant of the present invention possesses the following combination of characteristics:

(a) exhibits an erect growth habit,
(b) forms in abundance long lasting attractive double blossoms which are vermilion orange on the upper surface and scarlet pink on the under surface, and
(c) bears vigorous glossy vegetation.

The new variety well meets the needs of the horticultural industry for all uses, and is particulary well suited for use as ornamentation in parks and gardens.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meimainger variety.

BRIEF DESCRIPTION OF THE PHOTOGRAPH

The accompany photograph shows as nearly true as it is reasonably possibly to make the same, in a color illustration of this character, typical specimens of the plant parts of the new variety. The rose plants of the new variety were two years of age and observed during September while grafted on *Rosa froebelii* understock and growing in the open air at Cannet-des-Maures, Var, France.

Figures 1, 2, 3, 4, 5, 6, 7, 8, 9, 10, 11, 12, 13, 15, 16:
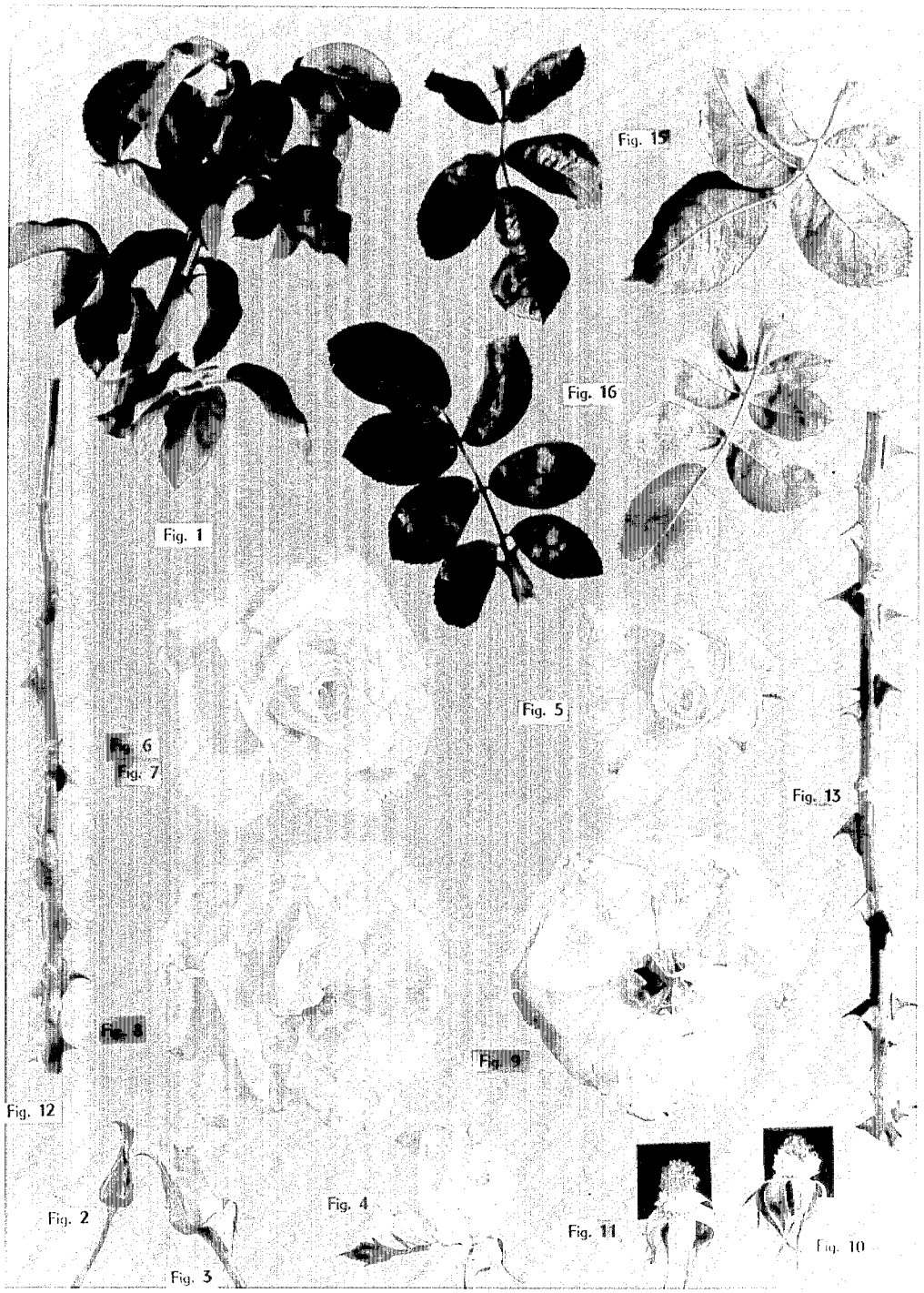
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.

FIG. 6/7 illustrates a specimen of a fully open flower — plan view — obverse;

FIG. 8 illustrates a specimen of a fully open flower immediately prior to petal drop — plan view — obverse;

FIG. 9 illustrates a specimen of a fully open flower immediately prior to petal drop — plane view — reverse;

FIG. 10 illustrates a specimen of a floral receptacle showing the arrangement of the stamens and pistils;

FIG. 11 illustrates a specimen of a floral receptacle showing the arrangement of the pistils (stamens removed);

FIG. 12 illustrates a specimen of a flower stem;

FIG. 13 illustrates a specimen of a main branch;

FIG. 14 is not illustrated;

FIG. 15 illustrates specimens of leaves with five leaflets showing the upper surface on the left and the under surface on the right; and FIG. 16 illustrates specimens of leaves with seven leaflets showing the upper surface on the left and under surface on the right.

DETAILED DESCRIPTION

The chart used in the identification of the colors is that of The Royal Horticultural Society (R.H.S. Colour Chart). The description is based on observations made during September of two years old plants while grafted on *Rosa froebelii* understock and growing in the open air at Cannet-des-Maures, Var, France.

Class: Hybrid Tea.

Plant:

*Height.*—Approximately 90 to 110 cm.

*Habit.*—Erect.

Branches:

*Color.*—Young stems: light green, Yellow-Green Group 146C, more or less shaded with a reddish tint. Adult wood: medium green, Yellow-Green Group 146B.

Leaves:

*Stipules.*—Adnate, pectinate, wide and linear.

*Petioles.*—Upper surface: grooved, reddish-brown on young foliage, and light green on adult foliage with glandular edges. Under surface: light green, bear some thorns mixed with aciculas.

*Leaflets.*—Number: 3, 5, and 7 (most often). Shape: oval. Serration: simple and regular. Texture: leathery. General appearance: ample and dense foliage with a glossy effect. Color (young foliage): Upper surface: medium green, Yellow-Green Group 147B, more or less shaded with a reddish tint. Under surface: medium green, Yellow-Green Group 147B, widely shade with red. Color (adult foliage): Upper surface: dark green, Yellow-Green Group 147A. Under surface: light green, Yellow-Green Group 147B, more or less shaded with a reddish tint.

Inflorescence:

*Number of Flowers.*—Generally one per stem.

*Peduncle.*—Straight, rigid, medium green, more or less shaded with red, it bears some glandular aciculas, its length is approximately 5 to 6 cm. on average.

*Sepals.*—Upper surface: tomentose, greenish, more or less shaded with red. Under surface: medium green, smooth with glandular edges which are more or less reddish in coloration, the outside petals are slightly appendiculated.

*Buds.*—Shape: conical. Length: approximately 4 to 5 cm. on average. Size: average. Color upon opening: Upper surface: azalea pink, Red group 41C, very luminous, darker at the petal edges. Under surface: chrome yellow, Yellow-Orange Group 14D, widely edged with scarlet pink, Red Group 43C.

*Flower.*—Shape: as a hollow cup. Diameter: approximately 11 to 12 cm. on average. Color (when opening begins): Upper surface: azalea pink, Red Group 41C, very luminous, darker at the petal edges. Under surface: chrome yellow, Yellow-Orange Group 14D, widely edged with scarlet pink, Red Group 43C. Color (when blooming): Upper surface: vermilion orange, Red Group 41B on the outside petals suffused with fire orange, Red Group 33B. Under surface: light scarlet pink, Red Group 43C on the outside petals. Color (at end of opening): Upper surface: vermilion orange, Red Group 41B, edged with signal red, Red Group 43A, and suffused with chrome yellow, Yellow-Orange Group 14C, at the base of the petals. Under surface: whitish tint, more or less suffused with light scarlet pink, Red Group 43C. Fragrance: strong and spicy. Lasting quality: long. Petal number: approximately 30 to 35 on average. Petal form: the outside petals tend to be flattened. Petal texture: firm. Petal drop: good. Stamen number: approximately 212 on average. Anthers: normal, bright yellow. Filaments: orange in coloration and of irregular heights. Pistils: approximately 136 on average. Stigmas: normal, straw colored. Styles: dark fuchsine, slightly twisted, of irregular heights, and tomentose at the base. Receptacle: light green, smooth at the dehiscence of the anthers, and in longitudinal section it is narrow and funnel shaped.

Development:

*Vegetation.*—Vigorous.

*Blooming.*—Abundant.

*Resistance to frost.*—Normal.

*Resistance to diseases.*—Very good.

I claim:

1. A new and distinct variety of Hybrid Tea rose plant characterized by the following combination of characteristics:

(a) exhibits an erect growth habit, (b) forms in abundance long lasting attractive double blossoms which are vermilion orange on the upper surface and scarlet pink on the under surface and exhibit a spicy fragrance, and (c) bears vigorous glossy vegetation;

substantially as herein shown and described, together with the parts thereof.

* * * * *